(12) United States Patent
Cheung

(10) Patent No.: US 8,893,782 B2
(45) Date of Patent: Nov. 25, 2014

(54) FLUID SENSOR AND METHOD OF USING SAME

(75) Inventor: Philip S. Cheung, Montesson (FR)

(73) Assignee: Schlumberger Technology Corporation, Sugar Land, TX (US)

( * ) Notice: Subject to any disclaimer, the term of this patent is extended or adjusted under 35 U.S.C. 154(b) by 277 days.

(21) Appl. No.: 13/579,942

(22) PCT Filed: Feb. 7, 2011

(86) PCT No.: PCT/EP2011/000555
§ 371 (c)(1),
(2), (4) Date: Oct. 17, 2012

(87) PCT Pub. No.: WO2011/101099
PCT Pub. Date: Aug. 25, 2011

(65) Prior Publication Data
US 2013/0037263 A1   Feb. 14, 2013

(30) Foreign Application Priority Data

Feb. 19, 2010   (EP) .................................. 10290084

(51) Int. Cl.
| | |
|---|---|
| G01V 3/08 | (2006.01) |
| E21B 47/10 | (2012.01) |
| G01N 27/06 | (2006.01) |
| G01N 33/28 | (2006.01) |

(52) U.S. Cl.
CPC ............ *G01N 27/06* (2013.01); *E21B 47/10* (2013.01); *G01N 33/2823* (2013.01)
USPC .................... 166/250.01; 324/324

(58) Field of Classification Search
USPC ..................... 166/250.01; 324/324
See application file for complete search history.

(56) References Cited

U.S. PATENT DOCUMENTS

| | | | |
|---|---|---|---|
| 3,449,640 A * | 6/1969 | Franklin | ............... 257/707 |
| 4,608,983 A | 9/1986 | Muller et al. | |
| 5,457,396 A | 10/1995 | Mori et al. | |
| 6,527,923 B2 | 3/2003 | Kirk et al. | |
| 6,801,039 B2 | 10/2004 | Fabris et al. | |
| 7,258,005 B2 | 8/2007 | Nyee | |
| 2009/0090176 A1 | 4/2009 | Toribio et al. | |
| 2009/0153155 A1 | 6/2009 | Chambon et al. | |
| 2009/0204346 A1 | 8/2009 | Xie | |

FOREIGN PATENT DOCUMENTS

| | | |
|---|---|---|
| DE | 19649366 | 5/1999 |
| EP | 1467060 | 10/2004 |
| GB | 2313196 | 11/1997 |

\* cited by examiner

*Primary Examiner* — William P Neuder
(74) *Attorney, Agent, or Firm* — Stephanie Chi; Jody DeStefanis

(57) ABSTRACT

A fluid sensor (and method) for determining at least one parameter of a fluid of a wellbore is provided. The fluid sensor has a base positionable in the wellbore, a base electrode operatively positionable in the insulation, and a raised electrode having at least one base portion and at least one raised portion. The base comprises insulation. The base portion is operatively positionable in the insulation. The at least one raised portion is positionable a distance above the base electrode such that a space is defined therebetween for the passage of the wellbore fluid therethrough. A voltage is applied across the base electrode and the raised electrode to generate a current therebetween whereby at least one parameter of the wellbore fluid may be determined. The fluid sensor is deployable into the wellbore via the downhole tool.

15 Claims, 4 Drawing Sheets

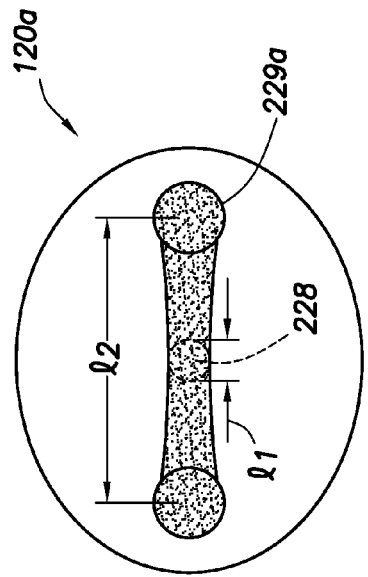
FIG.2A2
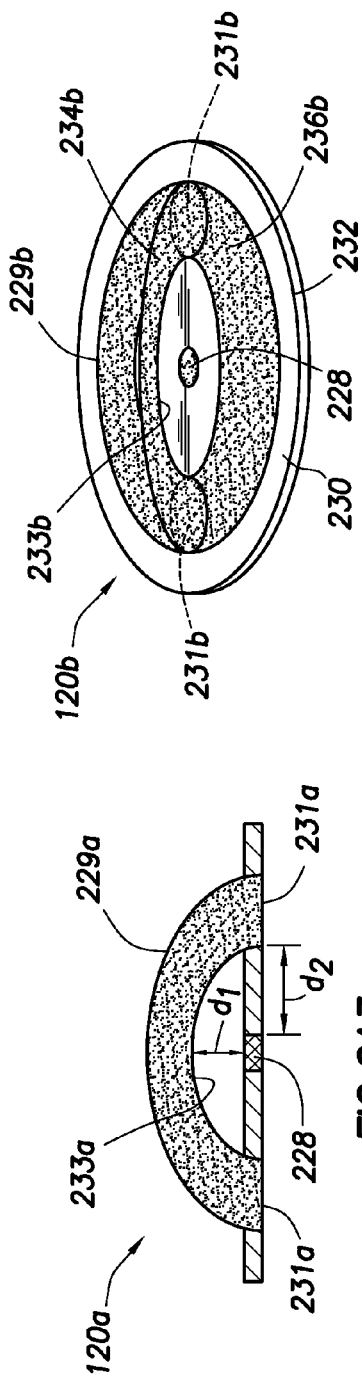
FIG.2B
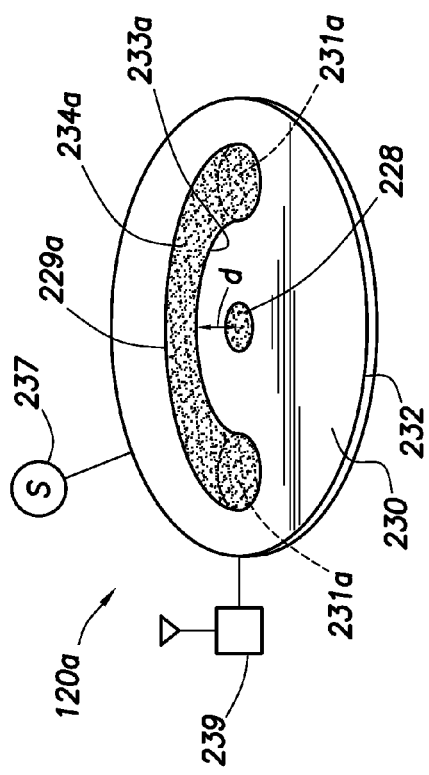
FIG.2A1
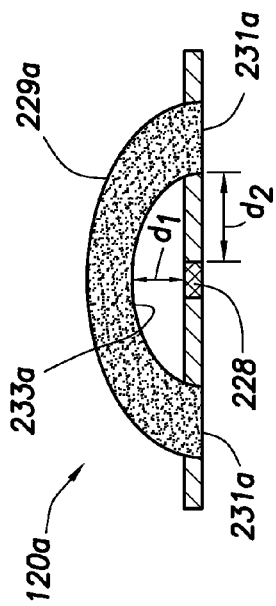
FIG.2A3

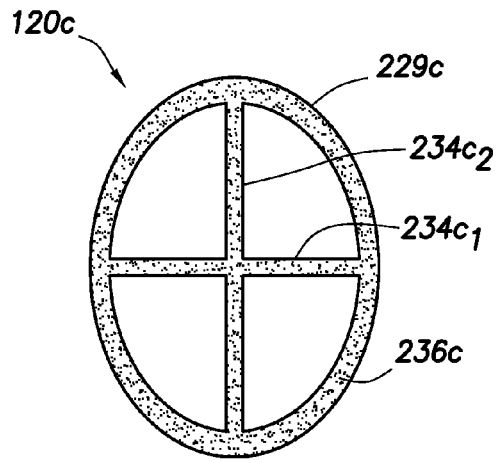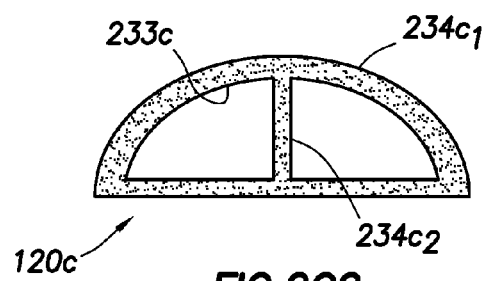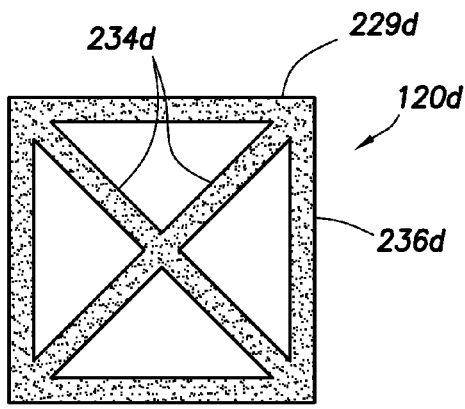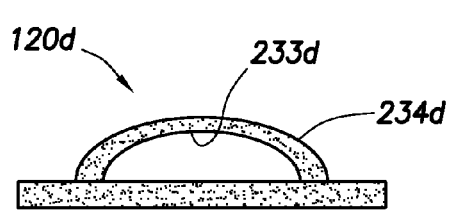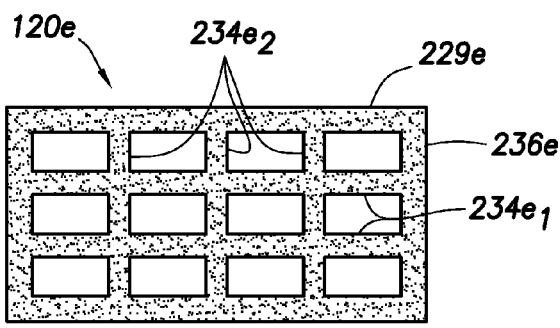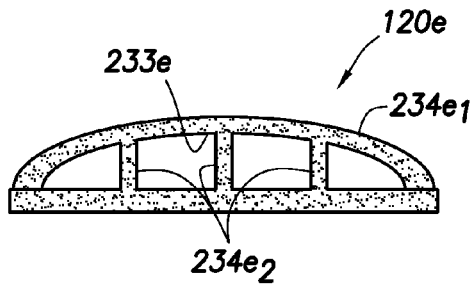

FLUID SENSOR AND METHOD OF USING SAME

BACKGROUND OF THE INVENTION

1. Field of the Invention

The present invention relates to techniques for determining fluid parameters. More particularly, the present invention relates to techniques for determining electrical parameters of downhole fluids.

2. Background of the Related Art

Oil rigs are positioned at wellsites for performing a variety of oilfield operations, such as drilling a wellbore, performing downhole testing and producing located hydrocarbons. Downhole drilling tools are advanced into the earth from a surface rig to form a wellbore. Drilling muds are often pumped into the wellbore as the drilling tool advances into the earth. The drilling muds may be used, for example, to remove cuttings, to cool a drill bit at the end of the drilling tool and/or to provide a protective lining along a wall of the wellbore. During or after drilling, casing is typically cemented into place to line at least a portion of the wellbore. Once the wellbore is formed, production tools may be positioned about the wellbore to draw fluids to the surface.

During drilling, measurements are often taken to determine downhole conditions. In some cases, the drilling tool may be removed so that a wireline testing tool may be lowered into the wellbore to take additional measurements and/or to sample downhole fluids. Once the drilling operation is complete, production equipment may be lowered into the wellbore to assist in drawing the hydrocarbons from a subsurface reservoir to the surface.

The downhole measurements taken by the drilling, testing, production and/or other wellsite tools may be used to determine downhole conditions and/or to assist in locating subsurface reservoirs containing valuable hydrocarbons. Such wellsite tools may be used to measure downhole parameters, such as temperature, pressure, viscosity, resistivity, etc. Such measurements may be useful in directing the oilfield operations and/or for analyzing downhole conditions.

In particular, it is often desirable to determine what types of fluids are present in the wellbore. Various techniques have been developed for measuring wellbore fluids as described, for example, in US Patent/Application No. 20090204346. Techniques have also been developed for using electrodes in downhole tools as described, for example, in US Patent/Application No. 20090090176 and 6801039. In some cases, electrodes have been used for measuring fluid properties as described, for example, in US Patent/Application Nos. 20090153155, 7258005, 5457396, 6527923, and 4608983.

Despite the development of techniques for measuring wellbore fluids and/or in the use of electrodes, there remains a need to provide advanced techniques for determining parameters of wellbore fluids using wellsite tools. It may be desirable to provide techniques that enhance downhole fluid measurements. It may be further desirable to provide techniques that reduce the effects of other components, such as conductive components, that may interfere with measurements. Preferably, such techniques involve one or more of the following, among others: accuracy of measurements, optimized measurement processes, reduced clogging, minimized components, reduced size, increased surface area for measurement, constant flow of fluids during measurement, optimized shape of measurement apparatus/system, real time capabilities, compatibility with existing wellsite equipment, operability in downhole conditions (e.g., at high temperatures and/or pressures), etc.

SUMMARY OF THE INVENTION

The present invention relates to a fluid sensor for determining at least one parameter of a fluid of a wellbore. The fluid sensor has a base positionable in the wellbore, a base electrode, and a raised electrode. The base comprises insulation. The base electrode is operatively positionable in the insulation. The raised electrode has at least one base portion and at least one raised portion. The base portion is operatively positionable in the insulation. The raised portion is positionable a distance above the base electrode such that a space is defined therebetween for the passage of the wellbore fluid therethrough. A voltage is applied across the base electrode and the raised electrode to generate a current therebetween whereby at least one parameter of the wellbore fluid may be determined.

The present invention also relates to a system for determining at least one parameter of a fluid in a wellbore. The system includes a downhole tool positionable in the wellbore and a fluid sensor. The fluid sensor has a base positionable in the wellbore, a base electrode, and a raised electrode. The base comprises insulation. The base portion is operatively positionable in the insulation. The raised electrode has at least one base portion and at least one raised portion. The raised portion is positionable a distance above the base electrode such that a space is defined therebetween for the passage of the wellbore fluid therethrough. A voltage is applied across the base electrode and the raised electrode to generate a current therebetween whereby at least one parameter of the wellbore fluid may be determined.

Finally, the present invention relates to a method for determining at least one parameter of a fluid in a wellbore. The method involves providing a fluid sensor. The fluid sensor has a base positionable in the wellbore, a base electrode, and a raised electrode. The base comprises insulation. The base electrode is operatively positionable in the insulation. The raised electrode has at least one base portion and at least one raised portion. The base portion is operatively positionable in the insulation. The raised portion is positionable a distance above the base electrode such that a space is defined therebetween for the passage of the wellbore fluid therethrough. The method further involves positioning a downhole tool into the wellbore with the fluid sensor thereon, receiving a downhole fluid between the pair of electrodes, applying a voltage across the pair of electrodes to generate a current therebetween, and determining the at least one fluid parameter from the generated current.

BRIEF DESCRIPTION OF THE DRAWINGS

So that the features and advantages of the present invention can be understood in detail, a more particular description of the invention may be had by reference to the embodiments thereof that are illustrated in the appended drawings. These drawings are used to illustrate only typical embodiments of this invention, and are not to be considered limiting of its scope, for the invention may admit to other equally effective embodiments. The figures are not necessarily to scale and certain features and certain views of the figures may be shown exaggerated in scale or in schematic in the interest of clarity and conciseness.

FIGS. 2A1-2E2 are schematic views of various versions of the fluid sensor of FIG. 1. FIGS. 2A1-2A3 and 2B show the fluid sensor with electrodes in a raised arched configuration. FIGS. 2C1-2C2 show the fluid sensor in a raised cross configuration. FIGS. 2D1-2D2 show the fluid sensor in a raised X configuration. FIGS. 2E1-2E2 show the fluid sensor in a raised grid configuration.

FIG. 3 is a flow chart depicting a method of determining downhole fluid parameters.

DETAILED DESCRIPTION OF THE INVENTION

Presently preferred embodiments of the invention are shown in the above-identified Figures and described in detail below.

Figure 1:
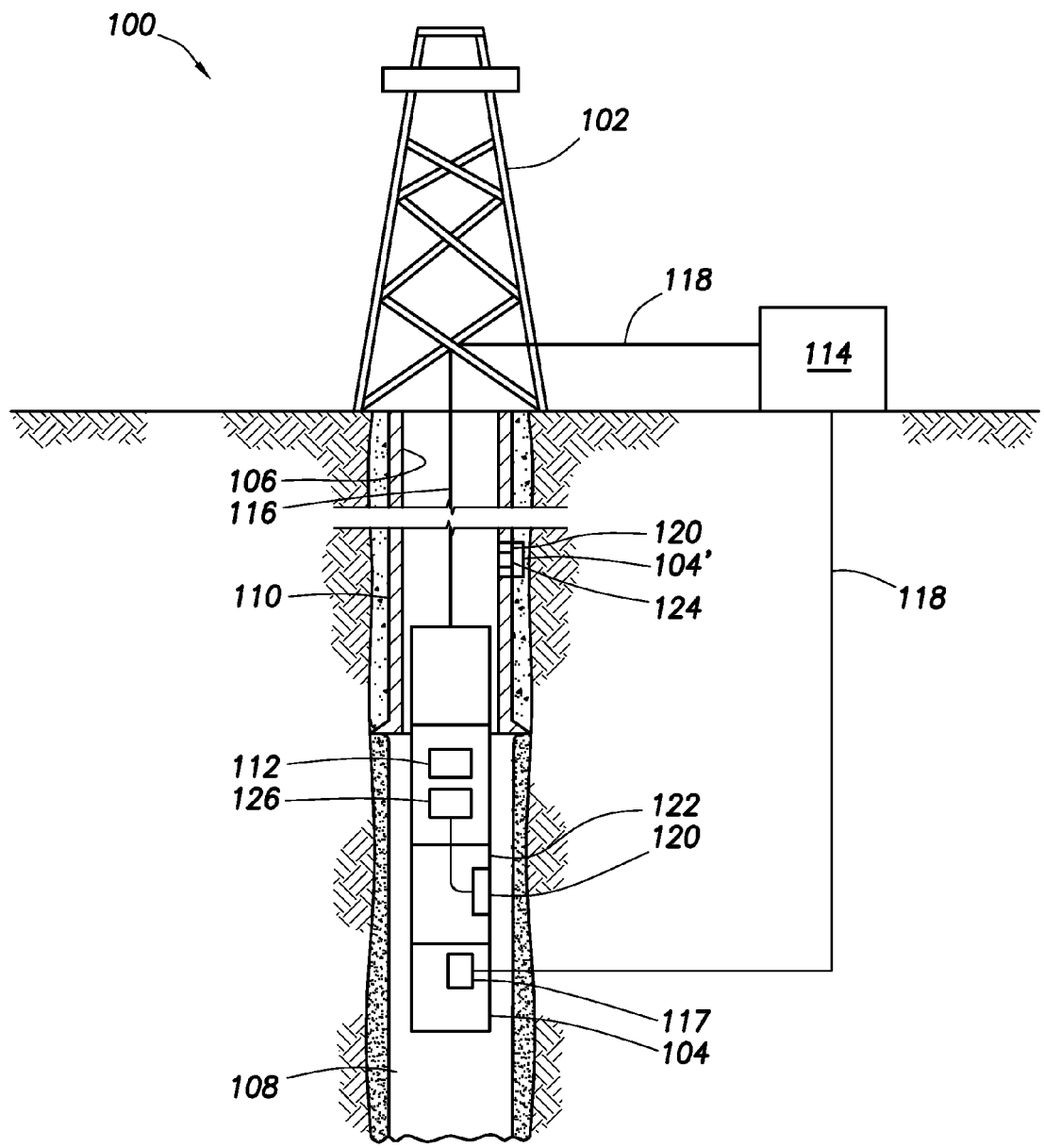
FIG. 1 is a schematic depiction of a system for determining downhole fluid parameters comprising a downhole tool positioned in a wellbore, and a fluid sensor on the downhole tool for determining fluid parameters.

FIG. 1 is a schematic view of a wellsite 100 having an oil rig 102 with a downhole tool 104 suspended into a wellbore 106 therebelow. The wellbore 106 has been drilled by a drilling tool (not shown). A drilling mud 108 has been pumped into the wellbore 106 and lines a wall thereof. A casing 110 has also been positioned in the wellbore 106 and cemented into place therein.

The downhole tool 104 is shown as a wireline logging tool lowered into the wellbore 106 to take various measurements. The downhole tool 104 has a conventional logging device 112 therein that may be provided with various sensors, measurement devices, communication devices, sampling devices and/or other devices for performing wellbore operations. For example, as the downhole tool 104 is lowered, it may use devices known in the art, such as resistivity or other logging devices, to measure formation properties.

The downhole tool 104 is operatively connected to a surface unit 114 for communication therebetween. The downhole tool 104 may be wired via the wireline 116 as shown and/or wirelessly linked via telemetry devices 117, such as conventional electromagnetic devices known in the art, for passing signals to a surface unit 114 as indicated by communication links 118. Signals may be passed between the downhole tool 104 and the surface unit 114 and/or other locations for communication therebetween.

The downhole tool 104 is also provided with a fluid sensor 120 for determining downhole fluid parameters. The fluid sensor 120 is preferably capable of determining parameters of downhole fluids, such as downhole mud (e.g., oil based), hydrocarbons, water and/or other downhole fluids. Additionally, the fluid sensor 120 is preferably capable of determining parameters of downhole fluids as the downhole tool 104 passes through the wellbore 106. Due to the harsh conditions of the downhole environment, the fluid sensor 120 is preferably positioned on the downhole tool 104 in such a manner that the fluid sensor is capable of receiving fluids as the downhole tool 104 passes through the wellbore 106, and that reduces clogging of such fluids as fluids pass through the fluid sensor 120. As shown, the fluid sensor 120 is positioned on an outer surface 122 of the downhole tool 104. The fluid sensor 120 may be recessed a distance below the outer surface 122 to provide additional protection thereto, or protruded a distance therefrom to access fluid. The fluid sensor 120 may also be positioned at various angles as desired.

The fluid sensor 120 is also depicted as being positioned on production monitoring devices 104'. The production monitors 104' may be conventional production monitors as known in the art. These production monitors 104' are typically positioned about the well as shown for monitoring the production of fluids through the wellbore 106. The fluid sensors 120 are positioned on an outer surface 124 of one or more of the production monitors 104'.

While the downhole tool 104 is depicted as a wireline tool 104 and a production monitor 104' with the fluid sensor 120 thereon, it will be appreciated that the fluid sensor 120 may be positioned downhole on a variety of one or more tools. For example, the fluid sensor 120 may be placed downhole on a drilling, coiled tubing, drill stem tester, production, casing, pipe, or other downhole tool. The fluid sensor 120 is preferably positioned about an outer surface of the downhole tool so that fluid may pass therealong for measurement thereof. However, it will be appreciated that one or more fluid sensors 120 may be positioned at various locations about the wellsite as desired for performing fluid measurement.

A power source 126 is operatively connected to the fluid sensor 120 for applying an AC voltage thereto at a frequency of between about tens of Hz to a few GHz. The power source 126 may be provided by a battery, power supply or other conventional means of providing power. In some cases, the power source 126 may be an existing power source used in the downhole tool. The power source 126 may be positioned, for example, in the downhole tool 104 and wired to the fluid sensor 120 for providing power thereto as shown. Optionally, the power source 126 may be provided for use with the fluid sensor 120 and/or other downhole devices. The power source 126 may be positioned within the fluid sensor 120 or separate therefrom. The fluid sensor 120 may also be wired or wirelessly connected to other features of the downhole tool, such as communication links, processors, power sources or other features thereof.

FIGS. 2A-2E show detailed views of various configurations 120a-e usable as the fluid sensor 120 of FIG. 1. Each fluid sensor 120a-e comprises a pair of electrodes 228,229a-e positioned in insulation 230 on a base (or pad) 232. Part or all of the base 232 may comprise the insulation 230. The base 232 may be adhered to the outer surface 122 of the downhole tool (e.g., 104 and/or 104' in FIG. 1) using any conventional means. The insulation 230 may be adhered to the base 232 using any conventional means. The insulation 230 is preferably a material, such as a polymide resin, capable of providing insulation about the electrodes 228,229a-e. The insulation 230 may be provided with a thin layer of copper thereon, with a layer of gold applied to the copper to prevent oxidation (not shown). The electrodes 228,229a-e may be applied into the insulation 230 in the desired configuration using, for example, printed circuit board technology, wet or dry etching, and/or other conventional electronics construction technique.

The electrodes 228,229a-e may be any conventional electrode capable of generating current across a fluid. A power source (e.g., power source 126 of FIG. 1) is operatively connected to the electrodes 228,229a-e for applying a voltage thereacross. The electrodes 228,229a-e are combined to form a capacitor for measuring current flowing therebetween. The electrodes 228,229a-e are preferably positioned such that capacitances are achieved between the surfaces of the electrodes 228,229a-e as wellbore fluids pass therebetween. As voltage is applied, a current flows out of one of the electrodes that can be measured.

The current from the electrodes may be used to determine various parameters. In an example involving a fluid passing between a pair of electrodes, an AC voltage V is applied between two parallel plates to generate a resultant current I that can be measured at either electrode. An impedance generated from the electrodes may consist of two capacitances in parallel, such as the capacitances between the electrodes interfacing with the wellbore fluid and interfacing with the insulation. The complex impedance Z can determined from the measured current I based on the following:

$$Z=|Z|\exp(i\phi_Z) \qquad \text{Equation (1)}$$

where its magnitude |Z| based on Ohms law and phase $\phi_Z$ are defined as follows:

$$|Z|=|V/I| \qquad \text{Equation (2)}$$

$$\phi_Z = \text{phase of } I \text{ relative } V \qquad \text{Equation (3)}$$

and where $\exp(i\phi_Z)$ based on Euler's formula is defined as follows:

$$\exp(i\phi_Z)=\sin\phi_Z+i\cos\phi_Z \qquad \text{Equation (4)}$$

The magnitude and phase of the impedivity (sometimes referred to as the complex impedivity) of a fluid $\zeta$ is defined as follows:

$$\zeta=|\zeta|\exp(i\phi_\zeta) \qquad \text{(Equation 5)}$$

Equation (5) may be derived from Z by the relations as follows:

$$|\zeta|=k|Z| \qquad \text{Equation (6)}$$

Equation (6) may also be written as follows:

$$|\zeta|=k|V|/|I| \qquad \text{Equation (7)}$$

The phase (or dielectric angle) of the fluid $\zeta$ is derived as follows:

$$\phi_\zeta=\phi_Z \qquad \text{Equation (8)}$$

where:
  $|\zeta|$ is the magnitude of impedivity,
  $\phi_\zeta$ is the phase angle of the impedivity, and
  k is a constant for the device.

The constant k may be measured empirically, for example, by measuring the impedance V/I between electrodes as a fluid of known impedivity is passed therethrough. The constant k may also be calculated from the geometry of the electrodes using conventional methods.

Data concerning the measured current may be used to determine fluid parameters, such as impedivity, resistivity, impedance, general conductivity, complex conductivity, complex permittivity, tangent delta, and combinations thereof, as well as other parameters of the wellbore fluid. The data may be analyzed to determine characteristics of the wellbore fluid, such as the type of fluid (e.g., hydrocarbon, mud, contaminants, etc.) A processor (e.g., logging device 112 of FIG. 1) may be used to analyze the data. Optionally, the data may be communicated to the surface unit 114 and/or other location for storage and/or analysis. Such analysis may be performed with other inputs, such as historical or measured data about this or other wellsites. Reports and/or other outputs may be generated from the data. The data may be used to make decisions and/or adjust operations at the wellsite. In some cases, the data may be fed back to the wellsite for real-time decision making and/or operation.

Preferably, the electrodes 228,229a-e of the fluid sensor 120 are configured to optimize measurement of fluid passing therebetween. The insulating base is preferably of a small dimension having a surface area of about 1 cm². The raised (i.e. arch) electrode fits within the base and has about the same overall dimensions. The base electrode is preferably smaller, having a surface are of a few square millimeters.

As shown in FIGS. 2A-2E, a portion of electrodes 229a-e are in a raised configuration relative to electrodes 228 to enable fluid flow therebetween. A voltage may be applied across the electrodes 228,229a-e. The voltage may be, for example, an AC voltage signal at a frequency of between about 10 Hz and 5 GHz. The electrodes 228,229a-e are preferably positioned with a space therebetween, to act as a capacitor with a current flowing thereacross. The electrodes are preferably configured for sensitivity to, for example, wellbore mud. The current flowing from either electrode 228, 229a-e may be measured as described above. The information gathered preferably provides information sufficient to determine various fluid parameters and/or to identify the type of fluid (e.g., hydrocarbon, mud, etc.) This information may be used for further analysis, for example to provide microresistivity imaging of the wellbore. The information may also be used to locate and/or characterize reservoirs.

The fluid sensor 120 may be operatively connected to devices for operation therewith. As shown in FIG. 2A1, a downhole sensor 237 may be provided to measure various wellbore parameters. A transceiver 239 may also be provided for communication with the fluid sensor 120. For example, the transceiver 239 may communicate wirelessly with the logging tool 112 (see FIG. 1). A communication link may also be provided with a wired connection between the fluid sensor 120 and the logging tool 112. The fluid sensor 120 may communicate with the surface unit 114 directly, or via the downhole tool 104.

FIGS. 2A1, 2A2 and 2A3 depict a fluid sensor 120a with a raised arch configuration. Electrode 228 is positioned in insulation 230 of base 232. Electrode 229a has two anchors 231a at each end thereof. The anchors 231a are positioned in insulation 230 of base 232. In this configuration, the electrode 229a has a raised portion 234a positioned a distance above the base 232 and electrode 228 to define a space 233a therebetween for the flow of fluid therethrough.

FIG. 2A2 is a plan view of the fluid sensor 120a of FIG. 2A1. As shown in this view, the electrode 228 is preferably positioned underneath a central portion of electrode 229a. The length l1 of the electrode 228 is preferably about 5 mm² or less. The length l2 of electrode 229a is preferably about 25 mm or less.

Figure 3:
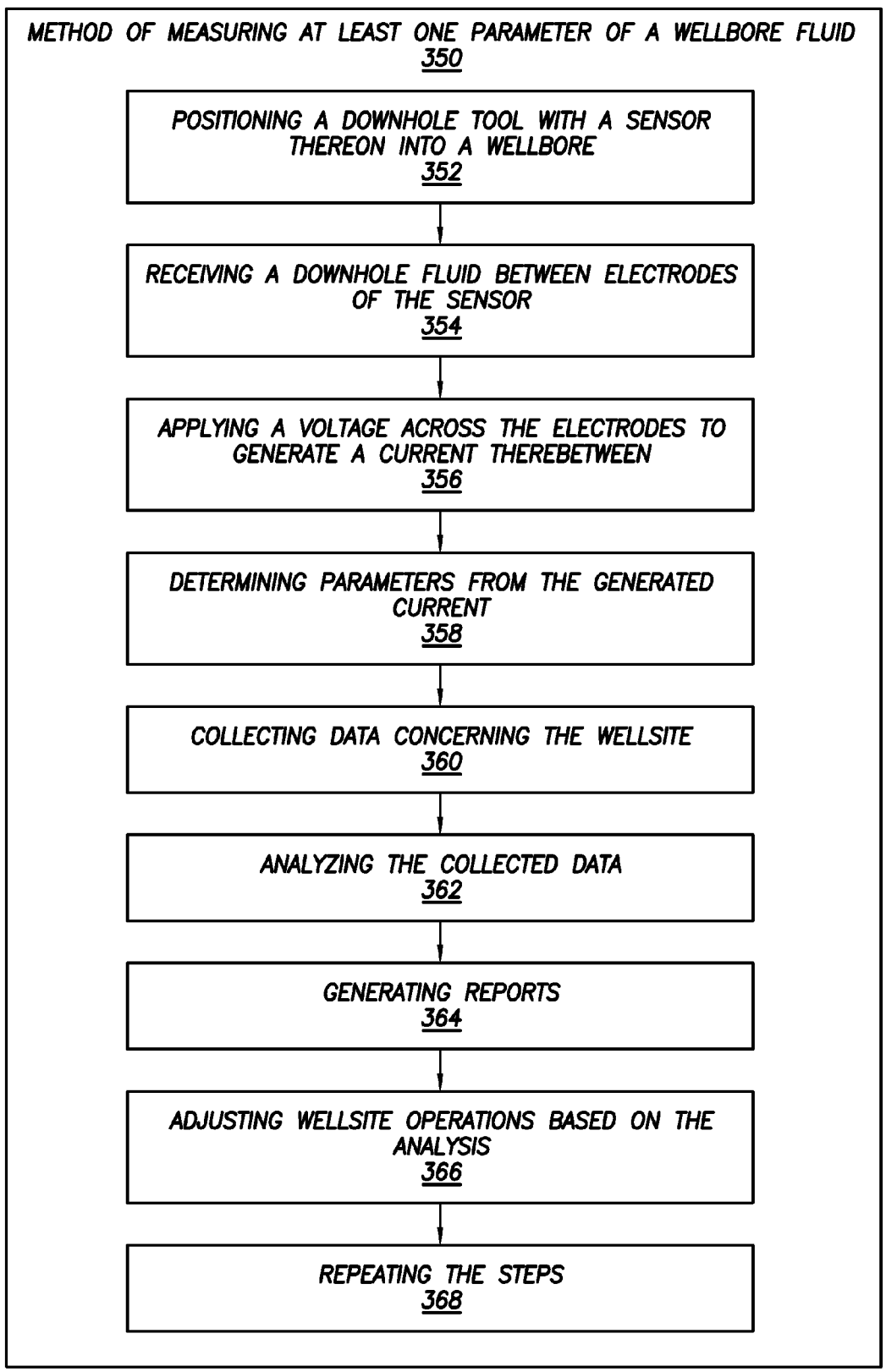

FIG. 2A3 shows an elevational view of the fluid sensor 120a of FIG. 2A1. A distance d1 is defined in a space 233a between the electrode 228 and the electrode 229a at its highest point as shown. The space between the electrodes in this raised direction is sufficient to prevent clogging, for example, about 2-3 mm. A distance d2 is defined between electrode 228 and anchor 231a as shown. Preferably, the distance d1 is smaller by a factor of about two or more than the distance d2, for example, at about 4-6 mm.

FIGS. 2B-2E2 depict various embodiments of the fluid sensor 120c-e having a raised portion 234b-e and a base portion 236b-e. The fluid sensors 120c-e may include a base 232 comprising insulation 230 as described, for example, with respect to FIG. 2A1, and an electrode 228 positioned in the insulation 230 on base 232 (not shown on FIGS. 2C1-2E2). The electrodes 229b-e are operatively connected in the insulation 230 of the base 232 in various raised configurations over electrodes 228 with a space 233b defined therebetween.

FIG. 2B shows an alternate version 120b of the raised arch fluid sensor 120a of FIGS. 2A1-2A3. This configuration is the same as the fluid sensor 120a, except that electrode 229b has a base portion 236b coupled to the raised portion 234b. The base portion 236b is an elliptical loop positioned in insulation 230 of base 232, and encircling electrode 228. Raised portion 234b may be anchored to the electrode 229b via anchors 231b. The raised portion 234b may be integral with the base portion 236b, or operatively coupled to the base portion 236b and/or electrode 229b via the anchors 231b. As shown in this configuration, the base portion 236b may act in conjunction with or in place of anchor 231b.

FIGS. 2C1-2C2 depict top and elevational views, respectively, of a fluid sensor 120c in a raised cross configuration. In this configuration, the electrode 229c has an oval portion 236c that forms a loop positioned in insulation 230 of base 232 (not shown), and two raised arches 234c1,c2 operatively connected to the oval base portion 236c. The two raised arches 234c1,c2 are operatively connected perpendicular to each other to form a cross as seen in the top view of FIG. 2C1. The raised arch 234c1 is depicted as being attached to the oval base portion 236c at the widest part thereof. The raised arch 234c2 is depicted as being attached to the oval portion 229c at the longest part thereof. As shown, the raised arches 234c1,c2 are unitary with each other and base portion 236c. A space 233c is defined between the electrodes 229c and 228 as shown in FIG. 2C2.

FIGS. 2D1-2D2 depict top and elevational views, respectively, of a fluid sensor 120d in a raised X configuration. In this configuration, the electrode 229d has a square base portion 236d that forms a loop positioned in insulation 230 of base 232 (not shown), and two raised arches 234d are operatively connected to the oval base portion 236d. The two raised arches 234d connect at a peak to form an X as seen in the top view of FIG. 2D1. The raised arches 234d are depicted as being attached to the square base portion 236d at the corners thereof. As shown, the raised arches 234d are unitarily with each other and base portion 236d. A space 233d is defined between the electrodes 229d and 228 as shown in FIG. 2D2.

FIGS. 2E1-2E2 depict top and elevational views, respectively, of a fluid sensor 120e in a raised grid configuration. In this configuration, the electrode 229e has an rectangular base portion 236e positioned in insulation 230 of base 232 (not shown), and multiple raised arches 234e1,e2 operatively connected to the rectangular base portion 236e. The two raised arches 234e1,e2 are operatively connected to form a grid as seen in the top view of FIG. 2E1. Two raised arches 234e1 are depicted as being attached to the rectangular base portion 236e at the longest part thereof. Three raised arches 234e2 are depicted as being attached to a short side of rectangular base portion 236e at the longest part thereof. As shown, the raised arches 234e1,e2 are unitarily with each other and base portion 236e. A space 233e is defined between the electrodes 229e and 228 as shown in FIG. 2E2.

The base 232 and/or insulation 230 thereon may be of any shape. The base 232 is preferably a loop positioned about the electrode 228. The shape of the looped base may be elliptical as shown in FIGS. 2A1-C2, square as shown in FIGS. 2D1-2 or rectangular as shown in FIGS. 2E1-2. Preferably, the electrode 228 is positioned centrally below the electrode 229b-e. Electrode 229b-e is preferably positioned such that portions of the electrode are positioned symmetrically about the electrode 228. The fluid sensors 120a-e may be positioned at a desired angle such that the electrodes 228,229a-e are positioned in a desired direction.

FIG. 3 is a flow chart depicting a method (350) of determining at least one parameter of a wellbore fluid. The method involved positioning (352) a downhole tool 104 with a fluid sensor 120 thereon into a wellbore 106 (see, e.g., FIG. 1). A downhole fluid 108 is received (354) between electrodes of the fluid sensor 120. A voltage is applied (356) across electrodes 228,229a-e of the fluid sensor 120 to generate a current therebetween (see, e.g., FIGS. 2A-2D). Parameters may be determined (358) from the current generated from the electrodes.

Data may be collected (360) concerning the wellsite. This data may be data from the fluid sensor 120, the downhole sensor 233, historical or other data. The collected data may be analyzed (362) and reports generated (364). Actions, such as adjusting wellsite operations, may be taken (366) based on the analysis. The steps of the method may be repeated (368) continuously or at discrete locations as the downhole tool 104 is moving through the wellbore. Various combinations of the steps of the method may be performed in a desired order using one or more downhole tools 104 and/or one or more fluid sensors 120.

It will be understood from the foregoing description that various modifications and changes may be provided. For example, the one or more fluid and/or other sensors may be positioned about the wellsite to measure and/or collect data.

This description is intended for purposes of illustration only and should not be construed in a limiting sense. The scope of this invention should be determined only by the language of the claims that follow. The term "comprising" within the claims is intended to mean "including at least" such that the recited listing of elements in a claim are an open group. "A," "an" and other singular terms are intended to include the plural forms thereof unless specifically excluded.

What is claimed is:

1. A fluid sensor for determining at least one parameter of a fluid of a wellbore, the fluid sensor comprising:
   a base positionable in the wellbore, the base comprising insulation;
   a base electrode operatively positionable in the insulation; and
   a raised electrode having at least one base portion and at least one raised portion, the at least one base portion operatively positionable in the insulation, the at least one raised portion positionable a distance above the base electrode such that a space is defined therebetween for the passage of the wellbore fluid therethrough;
   wherein a voltage applied across the base electrode and the raised electrode generates a current therebetween whereby at least one parameter of the wellbore fluid may be determined.

2. The fluid sensor of claim 1, wherein the at least one raised portion comprises an arch and the at least one base portion comprises a pair of anchors, each of the pair of anchors on opposite ends of the arch.

3. The fluid sensor of claim 2, wherein the at least one base portion forms a loop about the base electrode.

4. The fluid sensor of claim 1, wherein the at least one raised portion comprises a plurality of arches and wherein the at least one base portion forms a loop about the base electrode, the plurality of arches operatively connected to the base portion in a cross configuration.

5. The fluid sensor of claim 1, wherein the at least one raised portion comprises a plurality of arches and wherein the at least one base portion forms a loop about the base electrode, the plurality of arches operatively connected to the base portion in an X configuration.

6. The fluid sensor of claim 1, wherein the at least one raised portion comprises a plurality of arches and wherein the at least one base portion forms a loop about the base electrode, the plurality of arches operatively connected to the base portion in a grid configuration.

7. The fluid sensor of claim 1, further comprising a power source for providing the voltage.

8. The fluid sensor of claim 1, further comprising a processor for analyzing the current to determine the at least one fluid parameter.

9. The fluid sensor of claim 1, further comprising at least one wellsite sensor operatively connected thereto for determining at least one parameter of the wellbore.

10. The fluid sensor of claim 1, wherein the at least one parameter of the wellbore fluid is one of impedivity, resistivity, impedance, general conductivity, complex conductivity, complex permittivity and/or tangent delta, and combinations thereof.

11. The fluid sensor of claim 1, wherein the base is positionable downhole in the wellbore via a downhole tool.

12. The fluid sensor of claim 11, wherein the downhole tool is one of a drilling tool, a wireline tool, a production tool, monitoring tool, production monitor, a coiled tubing tool, a casing tool and combinations thereof.

13. A method for determining at least one parameter of a fluid in a wellbore, the method comprising:
providing a fluid sensor comprising:
- a base positionable in the wellbore, the base comprising insulation;
- a base electrode operatively positionable in the insulation; and
- a raised electrode having at least one base portion and at least one raised portion, the at least one base portion operatively positionable in the insulation, the at least one raised portion positionable a distance above the base electrode such that a space is defined therebetween for the passage of the wellbore fluid therethrough;

positioning a downhole tool into the wellbore with the fluid sensor thereon;
receiving a downhole fluid between the base and raised electrodes;
applying a voltage across the pair of electrodes to generate a current therebetween; and
determining the at least one fluid parameter from the generated current.

14. The method of claim 13, further comprising analyzing the at least one fluid parameter.

15. The method of claim 14, further comprising adjusting at least one wellsite operation based on the analyzed at least one fluid parameter.

* * * * *